(12) United States Patent
Kara et al.

(10) Patent No.: US 11,551,810 B2
(45) Date of Patent: Jan. 10, 2023

(54) METHOD FOR ACQUIRING AND FOR ALTERING A CONFIGURATION OF A NUMBER OF OBJECTS IN A PROCEDURE ROOM AND CORRESPONDING DEVICE

(71) Applicants: SIEMENS HEALTHCARE GMBH, Erlangen (DE); FRAUNHOFER GESELLSCHAFT ZUR FÖRDERUNG DER ANGEWANDTEN FORSCHUNG E.V., Mrinchen (DE)

(72) Inventors: Kerim Kara, Forchheim (DE); Jan Stallkamp, Munich (DE)

(73) Assignee: Siemens Healthcare GmbH, Erlangen (DE)

(*) Notice: Subject to any disclaimer, the term of this patent is extended or adjusted under 35 U.S.C. 154(b) by 198 days.

(21) Appl. No.: 16/959,221

(22) PCT Filed: Jan. 3, 2018

(86) PCT No.: PCT/EP2018/050128
§ 371 (c)(1),
(2) Date: Jun. 30, 2020

(87) PCT Pub. No.: WO2019/134743
PCT Pub. Date: Jul. 11, 2019

(65) Prior Publication Data
US 2020/0335207 A1    Oct. 22, 2020

(51) Int. Cl.
*G16H 40/20* (2018.01)
*G16H 40/67* (2018.01)
(Continued)

(52) U.S. Cl.
CPC ............ *G16H 40/20* (2018.01); *A61B 5/1113* (2013.01); *A61B 5/742* (2013.01); *A61B 5/746* (2013.01); *G16H 40/67* (2018.01)

(58) Field of Classification Search
CPC ...... G16G 40/20; G16G 40/67; A61B 5/1113; A61B 5/742; A61B 5/746; G16H 40/20; G16H 40/67
See application file for complete search history.

(56) References Cited

U.S. PATENT DOCUMENTS

| 8,571,710 B2 | 10/2013 | Coste-maniere |
| 10,717,194 B2 * | 7/2020 | Griffiths ............... A61B 34/35 |

(Continued)

FOREIGN PATENT DOCUMENTS

| CN | 205009236 U | 2/2016 |
| WO | WO2015023831 A1 | 2/2015 |
| WO | WO2017146890 A1 | 8/2017 |

OTHER PUBLICATIONS

International Search Report and the Written Opinion for International Patent Application PCT/EP2018/050128 dated Aug. 9, 2018.
(Continued)

*Primary Examiner* — Hoi C Lau
(74) *Attorney, Agent, or Firm* — Lempia Summerfield Katz LLC (57) ABSTRACT

The disclosure relates to a method for acquiring and for altering a configuration of a number of objects in a procedure room for planning and for collision avoidance during a medical procedure, wherein each object is represented by a virtual model, including a physical model of the object and a safety zone around the physical model. The physical model represents the configuration of the object and the safety zone represents a collision-prevention area for a movement of any of the objects during a medical procedure. The virtual models of the objects are placed at a position in a virtual model of the procedure room. Additionally, the configurations of the physical models during the medical procedure are computed and the configuration of the physical model of the corresponding object is altered when a collision during
(Continued)

the movement is determined. The disclosure further relates to a device for executing the method.

19 Claims, 3 Drawing Sheets

(51) Int. Cl.
    *A61B 5/11*     (2006.01)
    *A61B 5/00*     (2006.01)

(56) References Cited

U.S. PATENT DOCUMENTS

| | | |
|---|---|---|
| 2010/0094459 A1 | 4/2010 | Cho |
| 2012/0253515 A1 | 10/2012 | Coste-Maniere |
| 2013/0325030 A1 | 12/2013 | Hourtash |
| 2014/0163736 A1 | 6/2014 | Azizian |
| 2015/0005785 A1 | 1/2015 | Olson |
| 2016/0203282 A1 | 7/2016 | Azizian |
| 2016/0345929 A1 | 12/2016 | Azizian |
| 2017/0347979 A1* | 12/2017 | Fehre ............... G06F 30/13 |
| 2019/0054620 A1* | 2/2019 | Griffiths ............. G16H 50/50 |

OTHER PUBLICATIONS

Ladikos, Alexander, Selim Benhimane, and Nassir Navab. "Real-time 3D reconstruction for collision avoidance in interventional environments." International Conference on Medical Image Computing and Computer-Assisted Intervention. Springer, Berlin, Heidelberg, 2008. pp. 1-8.

Täubig, Holger, and Udo Frese. "A new library for real-time continuous collision detection." ROBOTIK 2012; 7th German Conference on Robotics. VDE, 2012. pp. 108-112.

\* cited by examiner

METHOD FOR ACQUIRING AND FOR ALTERING A CONFIGURATION OF A NUMBER OF OBJECTS IN A PROCEDURE ROOM AND CORRESPONDING DEVICE

The present patent document is a § 371 nationalization of PCT Application Serial No. PCT/EP2018/050128, filed Jan. 3, 2018, designating the United States, which is hereby incorporated by reference.

TECHNICAL FIELD

The present disclosure relates to a method for acquiring and for altering a configuration of a number (e.g., plurality) of objects in a procedure room for planning and for collision avoidance during a medical procedure, wherein each object is represented by a virtual model, including a physical model of the object and a safety zone around the physical model, the safety zone representing a collision-prevention area for a movement of any of the objects during a medical procedure. Furthermore, the disclosure relates to a device for executing the method.

BACKGROUND

In diagnostic and treatment environments, such as an interventional suite or an operating room of a hospital, there may be a plurality of medical devices. A medical device is an apparatus in particular for diagnosis, treatment, monitoring, therapy, or the like of a patient. Diagnosis, treatment, monitoring, therapy, or the like are in the following referred to as a medical procedure, respectively.

Exemplarily such a medical device is a mobile x-ray c-arm, a medical assistant robot, or a patient table. In particular, a medical device is understood to include devices which aid in diagnosing, treating, monitoring, therapy, or the like of a patient, such as a display, an x-ray shield, and the like. Some of these medical devices are electronically moveable. For instance, the medical devices move due to an assignment of a target position or configuration or they work and move automatedly.

For example, the medical devices, (automated or non-automated), exhibit comparatively little or no exchange of data or signals between them. As such, the interoperability of the medical devices for automated processes or automated procedures is comparatively low. This is, in particular, due to a difference in a task the respective medical devices are designed to perform or due to the fact that the medical devices are from different vendors. Consequently, if such a medical device moves or is moved, a collision with another medical device is possible, resulting in danger for the patient or for medical staff and may cause repairing costs. Moreover, this comparatively low interoperability also impedes pre-procedural planning for an, at least partial, automated use of the medical devices due to the lack of exchange of data or signals.

From "A New Library for Real-time Continuous Collision Detection" by H. Täubig and U. Frese in "Proceedings of the 7$^{th}$ German conference on robotics (ROBOTIK-2012)", an algorithm (KCCD-library, Kinematic continuous collision detection library) for industrial and humanoid robots is presented, which uses convex hulls as a volume representation of the body of a robot, wherein the convex hulls are based on the robots current configuration. For determining a collision, a (swept) volume covered by the convex hull of the respective robot's body parts during a motion in an interval is determined and a distance between the determined swept volumes is computed. Therein the intervals are based on a joint angle, a joint angle velocity, a latency, a worst-case deceleration and joint angle uncertainties.

In WO 2015/023831 A1, a system and a method are disclosed for coordinated motion with a medical device including least one moveable element, and with at least one processor. Therein any of the processors uses a shared interface to access services. A token service provides movement tokens for the medical device through the shared interface. The medical device is configured to plan and execute a motion of one movable element based on the movement token, configuration data, kinematic data, or planned motion data.

From "Real-time 3D Reconstruction for Collision Avoidance in Interventional Environments" by A. Ladikos, S. Benhimane and N. Navab in "International Conference on Medical Image Computing and Computer-Assisted Intervention", Springer, 2008, a real-time reconstruction system is known, which predicts collision by building a 3D-representation of all objects in a room. The system includes a number of cameras, whose images are used for reconstructing the 3D-representation. Further, safety zones around objects in the room are computed.

In US 2012/0253515 A1, a method and an apparatus for surgical planning is disclosed, providing planning of entry port placement and/or robot position for laparoscopic and other minimal invasive surgery. For this purpose, a model of the surgical site is created, wherein image data of a patient is processed to accomplish such planning.

SUMMARY AND DESCRIPTION

It is an object of the present disclosure to provide a method, to improve the interoperability of medical devices in view of safety of a medical procedure and planning. Furthermore, it is an object of the present disclosure to provide a device for executing the method.

The scope of the present disclosure is defined solely by the appended claims and is not affected to any degree by the statements within this summary. The present embodiments may obviate one or more of the drawbacks or limitations in the related art. The specifications relating the method apply analogously to the system and vice versa.

The method is used for acquiring and for altering a configuration of a number (e.g., plurality) of objects in a procedure room for planning and for collision avoidance during a medical procedure. In particular, a medical procedure is a procedure for diagnosis, treatment, monitoring, or therapy of a patient.

Each object is represented by a virtual model, the virtual model including a physical model representing the configuration of the object and a safety zone, wherein the safety zone represents a collision prevention area for a movement of any of the objects during a procedure.

The virtual models of the objects are placed at a position in virtual model of the room. Further, the configurations of the physical models during the medical procedure are computed and, when a collision during the movement is determined, the configuration of the respective physical model is altered, in particular, such that a collision is avoided.

The configuration of an object is a characteristic selected from the object's shape, its position, if applicable the position of a joint of the object, the velocity of a moving part of the object, its orientation, the relative position of parts of the object in respect to each other, and/or a characteristic derived therefrom. The configuration of a physical model or its respective virtual model analogously is a characteristic selected from the respective model's shape, position, if applicable the position of a joint of the model, the velocity of a movable part of the model, its orientation, the relative position of parts of the respective model in respect to each other, and/or a characteristic derived therefrom. To configure an object, a physical model or a virtual model is here to adjust the configuration of the object, of the physical model, or of the virtual model, respectively.

In particular, a collision of the virtual models is determined, if the safety zones of the respective virtual models overlap or touch. Therein a virtual model is either the virtual model of an object or of the room. For this purpose, the KCCD-library as mentioned above is used, especially. Thus, the safety zone (convex hull) of an object is especially based on the respective object's configuration. Therein, however, the KCCD-library is altered for (diagnosis and treatment) environments in a procedure room. For example, the safety zone of the respective virtual model of an object is adjusted to increase the comfort of a patient. Further, the KCCD-library is altered such that a number of objects are considered for the determination of a collision, in particular by placing the virtual models of the respective objects in a shared, global coordinate system.

In particular, in order to avoid a collision, a velocity of the virtual model of the respective object is diminished or its movement stopped. Consequently, a collision between the virtual models of the respective objects as well as a collision between the virtual models of an object and the virtual model of the room, in particular its wall or ceiling, may be determined and avoided.

The virtual model of the room may be used as the shared, global coordinate system for the virtual models of the respective objects. Alternatively, a shared global coordinate system is predefined, and the virtual models of the room and the objects are positioned within accordingly. Advantageously, by this means it is possible to determine a relative position of the virtual models with respect to each other.

In an expedient embodiment, the physical model of a medical device is stored in a database and is retrieved for the computation when the medical device is registered, wherein the corresponding virtual model represents one of the objects in the procedure room. Therein, the configuration of the virtual model corresponds to the configuration of the corresponding object.

The registration of the medical device to a controller is, for example, done automatically by the controller, when the medical device is connected to the controller, or alternatively by a user input. Consequently, the physical model of the corresponding medical device and respectively the corresponding virtual model are included in the computation when the medical device is registered. For planning a medical procedure, (e.g., when the respective device is not yet connected to the controller), the respective model is retrieved for the computation from the database as needed.

Alternatively, the physical model or virtual model or data necessary to compute the respective model is transmitted from the medical device to a controller, in particular, when requested from the corresponding medical device by the controller.

For the physical model, a kinematic description of the object, (e.g., by so called Denavit-Hartenberg parameters), may be coupled to a corresponding CAD-model of the object. Therein, the safety zone of the corresponding virtual model is set by a default value, a user input, or by computation.

In particular, within the computation of the configuration of the physical models of the respective objects, only the configuration of physical model of those medical devices are altered when a collision is determined, which are connected to the controller.

Expediently, during a medical procedure, a device signal including data about the configuration of the respective medical device is received, in particular, by the controller, and the configuration of the physical model of the medical device is altered according to the received device signal.

Exemplarily, the device signal also includes an information about a use-case of the respective medical device. Therein, the use-case of a medical device represents its current status in view of its activity, such as "active," "inactive," "needle insertion," or "recording medical image."

Advantageously, by the device signal, the corresponding virtual models are altered according to the current configuration of the objects.

The device signal is, for example, sent by the respective device after a pre-defined time interval such as each 50 milliseconds (ms). The device signal may be sent when the configuration or the use-case of the respective medical device has changed, or when a target configuration is assigned to the medical device, exemplarily by a user input. By this method, the physical model of an object is altered accordingly in real-time.

Further, if a medical device provides and/or uses its own (device) coordinate system, its configuration in the device coordinate system is transformed into the global coordinate system. Consequently, the current position of the virtual models of the medical devices, with respect to each other, is derived.

In summary, the virtual models are dynamic virtual models. In particular, a change in the configuration of an object results in an according change of the configuration of the corresponding virtual model.

In an advantageous embodiment, a control signal for the control of the configuration, (e.g., the orientation, position, or velocity), of the respective medical device is generated during a medical procedure when a collision of the virtual model of the corresponding medical device is determined in the computation.

Additionally, a warning signal, such as an acoustical signal, for the medical staff or the patient may be generated and output.

Exemplarily for preventing a collision, prior to configuring a medical device according to a target configuration, (e.g., by a corresponding control signal), it is determined by the target configuration and the corresponding virtual models if the corresponding safety zone overlaps with or touches another safety zone. Alternatively, while the configuration of the medical device and the corresponding virtual model is being altered, (e.g., due to a corresponding control signal), it is determined if the corresponding safety zone overlaps with or touches another safety zone.

In an advantageous embodiment, a virtual model of the patient is derived from medical data, such as CT-Scans or ultrasound-images, wherein the virtual model represents the respective object in the procedure room. Further, the virtual model of the patient is positioned accordingly in the virtual model of the room. By this method, advantageously, an expedient position of the patient for a medical procedure may be computed and planned before the medical procedure. Alternatively, an expedient configuration, (e.g., a movement relative to the patient), of a medical device, (e.g., an x-ray c-arm), is determined and, if applicable, planned by this method.

Further, including the virtual model of the patient based on his/her medical data facilitates an intra-procedural image registration, e.g., as a virtual model of the patient. For instance, an orientation and position of the virtual model of an ultrasound-probe may be used to register and/or compare the measured data to a 3D-image, which was taken before the procedure, and to the therefrom derived virtual model of the patient.

According to a particular advantageous development, the respective medical device is configured according to the corresponding virtual model, e.g., without a collision. For this purpose, the control signal is used and (e.g., output) transmitted to the respective medical device. The control signal may be output in real-time, e.g., as soon as a collision is determined. In summary, when a collision of objects is determined, the configuration of the respective virtual model or models are altered, and the respective objects are configured, in particular moved or positioned, accordingly. For this purpose, the control signal is generated and subsequently output to the corresponding medical device, which in particular is connected to the controller. Consequently, the determined collision is avoided.

For example, a medical device is moved aside to provide space for medical staff when inactive or not in use.

In an advantageous embodiment, the dimensions of the safety zone are varied during a movement of the respective physical model. In particular, the safety zone is a dependent on the velocity of the physical model or of a moving part of the physical model. Exemplarily, a faster moving virtual model or, respectively, a moving part of the virtual model corresponds to a larger safety zone. A comparatively slow moving or stopped respective physical model corresponds to a comparatively small safety zone resulting, for example, in an increased operability or liberty of movement.

Alternatively or additionally, the dimensions of the safety zone around the physical model of an object may be dependent on the type of the object or its model, respectively. For example, a patient table requires a smaller safety zone than medical staff.

Further alternatively or additionally, the dimensions of the safety zone around the physical model of an object depend on a use-case of the respective virtual model. Exemplarily, a medical assistant robot requires a comparatively small safety zone for a needle insertion into a patient, otherwise however, the dimensions of its safety zone is, exemplarily, comparatively large.

Additionally or alternatively, the dimensions of the safety zone around the physical model of an object are dependent on a latency of an object, which is connected to the controller. By this method, the dimensions of the safety zone of the respective virtual model are advantageously comparatively large for a comparatively large processing duration of the controller.

Furthermore, according to a suited development, the virtual models of the objects and the room are displayed on a display device, e.g., in real-time. By this method, a view obstructed by an object may be displayed for the medical staff. Additionally, telemedicine and remote assistance is facilitated. The display device may be represented by a corresponding virtual model and thus included in the computation, as well.

According to an expedient embodiment, a device for acquiring and for altering a configuration of a number of objects in a procedure room for planning and for collision avoidance during a medical procedure includes a controller for executing the method in one of the variations described above.

Therein at least one object is a medical device, which is connected to the controller. In certain examples, a signal, (e.g., control signal), may be transmitted to the connected medical device.

The device, or respectively all connected medical devices, may only be connected to the controller. In other words, there is no connection in between the medical devices. The controller is a central unit by which all signals are received or sent. By this configuration, the controller may convert signals from medical devices from different vendors. In particular, the controller further provides a generic interface, (e.g., based on open source communication protocols), which is suited for different types of medical devices and for medical devices of different vendors. Advantageously, it is made possible to extend the above method for further medical devices.

According to a development, the device for acquiring and for altering a configuration of a number of objects in a procedure room for planning and for collision avoidance during a medical procedure further includes a tracking device that captures an object not connected to the controller. Further, the tracking device sends a tracking signal including data about the configuration of the non-connected object to the controller.

The physical model and/or the virtual model of such a non-connected (unconnected) object are, in particular, either computed based on the tracking signal. Alternatively, a suited physical or virtual model is chosen from the virtual models, which are stored in the database and altered according to the received tracking signal. In certain examples, the model is chosen by a user input or determined by an algorithm. In certain examples, the tracked object is registered to the controller.

Analogously to the device signal, the tracking signal is sent after a pre-defined time interval or when the configuration of the tracked object has changed. In this arrangement, the physical model of the object is altered accordingly in real-time.

In particular, by the tracking signal, the corresponding virtual models of objects, which are not connected to the controller, are altered according to the current configuration of the objects.

In certain examples, by the tracking device, medical staff is also represented by a corresponding virtual device.

In particular, each object, including the tracking device and the display device, is identified, in particular, by the device signal, the tracking signal or a user input, respectively, and assigned to its corresponding virtual model. Exemplarily, each object or device in the procedure room is assigned a unique identification number during its registration, wherein the respective identification number corresponds to the respective virtual model and wherein the identification number of a signal representing the identification number is included in the device signal and/or in the control signal.

A virtual model of the tracking device and the virtual model of the procedure room include analogously to the virtual model of the objects a physical models and a safety zone. The virtual model of the tracking device is placed at a position in the virtual model of the procedure room or, respectively, in the global coordinate system, accordingly.

All virtual models may be included in the computation, such that, advantageously, a collision of a unconnected object, the tracking device, the patient, the display device, the procedure room (e.g., the wall or ceiling), or a medical device is prevented.

The advantages of this disclosure consist in that the virtual models of objects in the room, including a patient and a tracking device, and the computation of the configuration of the virtual models is used for a pre-procedural planning of the procedure. Further, by the physical models and the computation of their configuration, a collision is avoided by configuring the respective physical object according to the corresponding virtual model. Thus, a danger for the medical staff or the patient, as well as a damage of the respective medical devices, is prevented. Further advantageously, the current position of the virtual models of the object is displayed, in particular, in real-time. Because electronically configurable as well as not electronically configurable medical devices may be used with this method, an interoperability of the medical devices is improved by the method and the device. Thus, the collision avoidance as well as the planning has as a result of automating the configuration of the objects during a procedure and the automation of a workflow of the respective medical procedure.

BRIEF DESCRIPTION OF THE DRAWINGS

In the following, embodiments of the present disclosure are explained with reference to the attached drawings.

Corresponding parts are provided with the same reference numerals in all figures.

DETAILED DESCRIPTION

Figure 1:
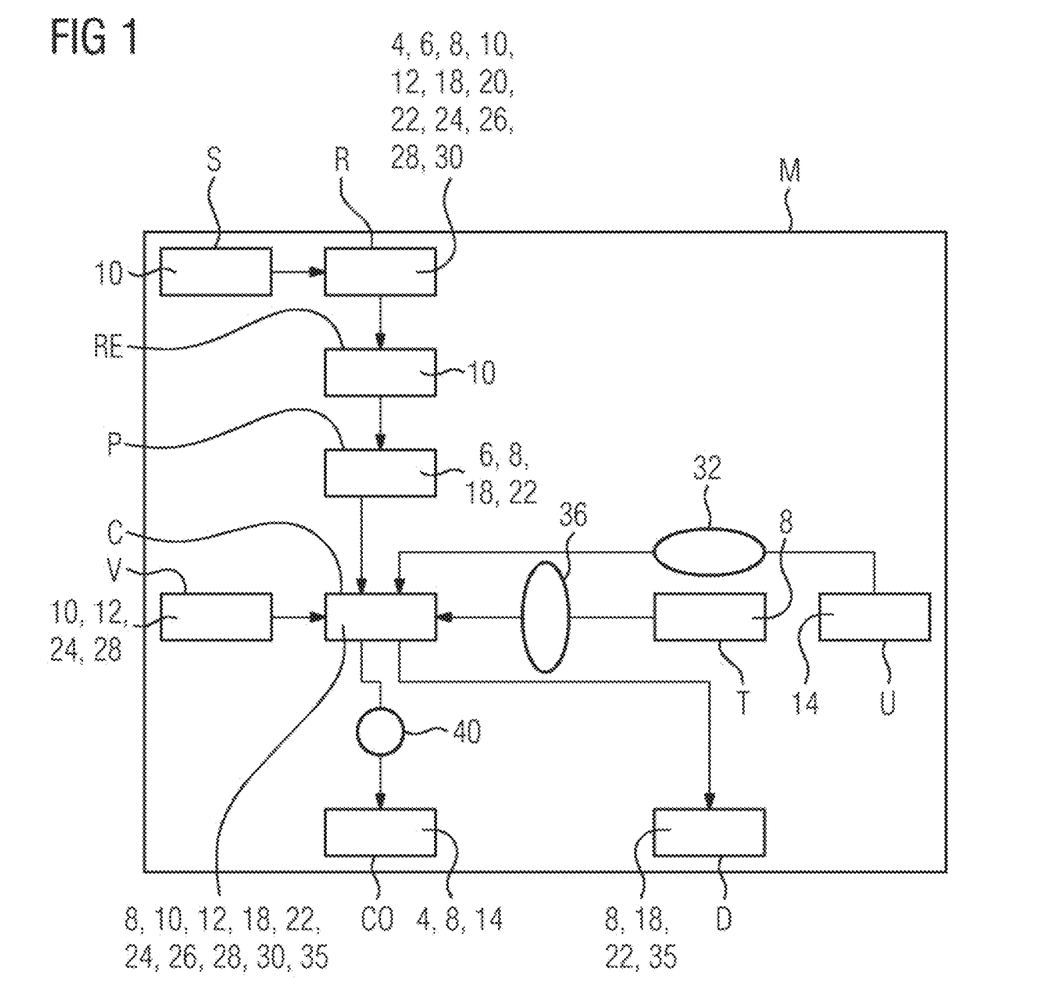
FIG. 1 depicts a flowchart diagram illustrating one embodiment of a method for acquiring and for altering a configuration of a number of objects in a procedure room for planning and for collision avoidance during a medical procedure, wherein each object as well as the procedure room is represented by a respective virtual model, and wherein a configuration of the virtual models is changed when a collision is determined.

The flowchart diagram of FIG. 1 depicts a method M for acquiring and for altering a configuration of a number (e.g., plurality) of objects 4 in a procedure room 6 for planning and for collision avoidance during a medical procedure. Therein, in a representation R, each object 4 is represented by a virtual model 8. Each virtual model 8 includes a physical model 10, representing the configuration of the corresponding object 4, in particular, its shape, its position, if applicable the position of its joint, the velocity of its movable part, its orientation, or its relative position of movable parts in respect to each other. Additionally, the virtual model 8 includes a safety zone 12 around the corresponding physical model 10, wherein the safety zone 12 represents a collision prevention area for a movement of any of the objects 4 during a medical procedure.

Therein, the physical model 10 of a medical device 14, with the corresponding virtual model 8 representing one of the objects 4 in the procedure room 6, is stored in a database within a storing-act S. The physical model 10 is retrieved from the database in a retrieving-act RE. The physical model 10 of the corresponding medical device 14 is retrieved from the database when the medical device 14 is registered to a controller 16 for executing the method M. According to this embodiment, the medical device 14 is connected to the controller 16 and automatically registered. In an alternative embodiment where only a planning of a medical procedure occurs and, in particular, the corresponding medical device 14 is not connected to the controller 16, the physical model 10 is retrieved from the database as needed.

Moreover, a virtual model 18 of a patient 20 is derived from his or her medical data, wherein the virtual model 18 represents an object 4 in the procedure room 6.

Further, in a placement-act P, the respective virtual models 8 of the objects 4 as well as the virtual model 18 of the patient 20 are placed in a virtual model 22 of the procedure room 6. Therein, the virtual model 22 of the procedure room 6 is used as a shared (e.g., common) coordinate system for the virtual models 8 of the objects 4. In other words, if applicable, the coordinate systems of the respective virtual models 8 of the corresponding objects 4 are transformed into the shared coordinate system. The virtual models 18, 22 of the patient 20 and the procedure room 6 analogously include a physical model 24, 26 and a safety zone 28, 30, respectively.

In a computation-act C, the configurations of the physical models 10, 24, 26 during the medical procedure are computed and the configuration of the respective physical model 10 of a medical device 14 is altered when a collision during a movement is determined. Herein, a collision of the virtual models 8, 18, 22 is determined when the safety zones 12, 28, 30 of the respective virtual models 8, 18, 22 overlap or touch.

Therein, the dimension of the safety zone 12, 28 of the respective virtual models 8, 18 is varied during a movement of the respective physical model 10, 24 (e.g., Variation V). In other words, the dimensions of the safety zone 12, 28 are dependent on a velocity of the respective physical model 10, 24.

Further, within an updating-act U, a medical device 14 connected to the controller 16 sends a device signal 32. The device signal 32 includes data about the configuration of the respective medical device 14. The device signal 32 is received by the controller 16 and the corresponding physical model 10 is altered according to the received device signal. The device signal 32 is generated and sent by the medical device 14 when its configuration or its use-case has changed, or when it is assigned a target configuration.

Additionally, within a tracking-act T, a tracking device 34 connected to the controller 16 captures medical devices 14, which are not connected to the controller 16, or the patient 20. The tracking device 34 sends a tracking signal 36 with data about the configuration of the medical devices 14 or of the patient 20 to the controller 16. The virtual model 8 or 18 is altered according to the corresponding tracking signal 36 within the computation-act C. A virtual model of the tracking device is also retrieved from the database and retrieved for the computation-act C.

Within a visualization-act D, a display device 38 is connected to the controller 16 and displays the virtual models 8, 18, 22 in real-time.

In the computation-act C, the configurations of the physical models 10, 24, 26 during the medical procedure are computed and altered such that the collision is prevented when a collision of the virtual models 8,18,22 is determined. Additionally, a control signal 40 for the control of the configuration of the respective medical device 14 is generated and transmitted to the medical device 14, such that the medical device 14 is configured within a configuration-act CO according to the corresponding virtual model 8. Consequently, a collision of the corresponding medical device 14 with the patient 20 or with the procedure room 6 is prevented.

Figure 2:
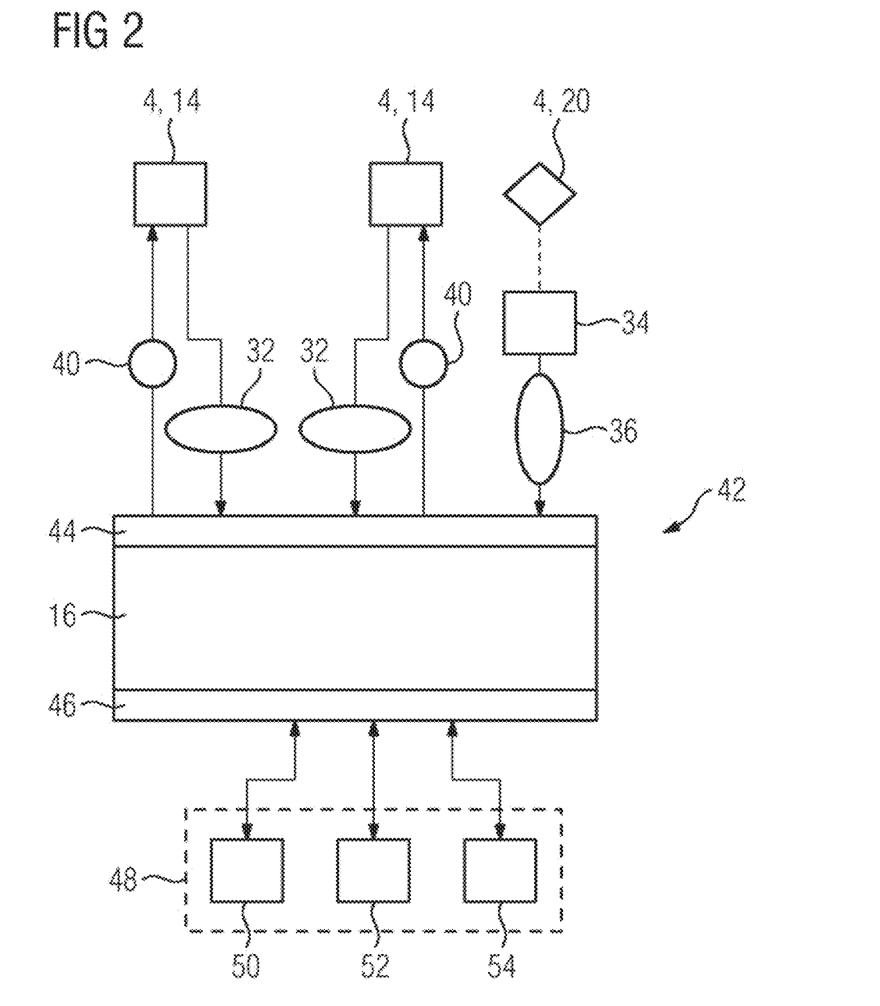
FIG. 2 schematically depicts in a block diagram an example of a device with a controller, wherein the controller includes two interfaces for medical devices and for a storage device, respectively, and wherein a software for collision avoidance and a visualization software is stored on the storage device.

FIG. 2 depicts in a block diagram a device 42 for executing (performing) the above described method M. The device 42 includes the controller 16. The controller 16 includes a first interface 44 and a second interface 46. Two medical devices 14 are connected to the controller 16 by the first interface 44. The device signal 32 is sent by the respective medical device 14 via the first interface 44 to the controller 16. The controller 16 on the other hand generates control signal 40 and transmits the control signal 40 to the respective medical device 14 via the first interface 44.

Further, the tracking device 34 is connected to the controller 16 via the first interface 44 as well. The tracking device 34 tracks a patient 20 or additionally a medical device 14, which is not connected to the controller 16.

A computer readable storage device 48 is connected to the controller 16 by the second interface 46. On the storage device, there is software for collision avoidance 50 and visualization software 52 for displaying the virtual models 8, 18, 22 on the display device 38 or for planning a medical procedure stored. Furthermore, an additional software 54 is stored on the storage device. Exemplarily, the additional software 54 is used for image registration and fusion, motion compensation, augmented reality, or smart path planning. Further exemplarily, the additional software 54 derives data from the respective virtual models, in particular for surgical navigation. Therein the software 50, 52, 54 is executed by the controller 16. In an alternative embodiment, the storage device 48 is integrated in the controller 16.

In summary, the controller 16 is a central unit. That means that the medical devices 14, the tracking device 34, and the display device 38 are only connected to the controller 16 by the respective interfaces 44, 46. Further, the software 50, 52, 54 only exchanges data with the controller 16. Any additional software 52, which may be integrated at a later time, does not need to integrate the virtual models 8, 18, 22 or the virtual model of the tracking device 35, because the virtual models already are stored in the database.

Figure 3:
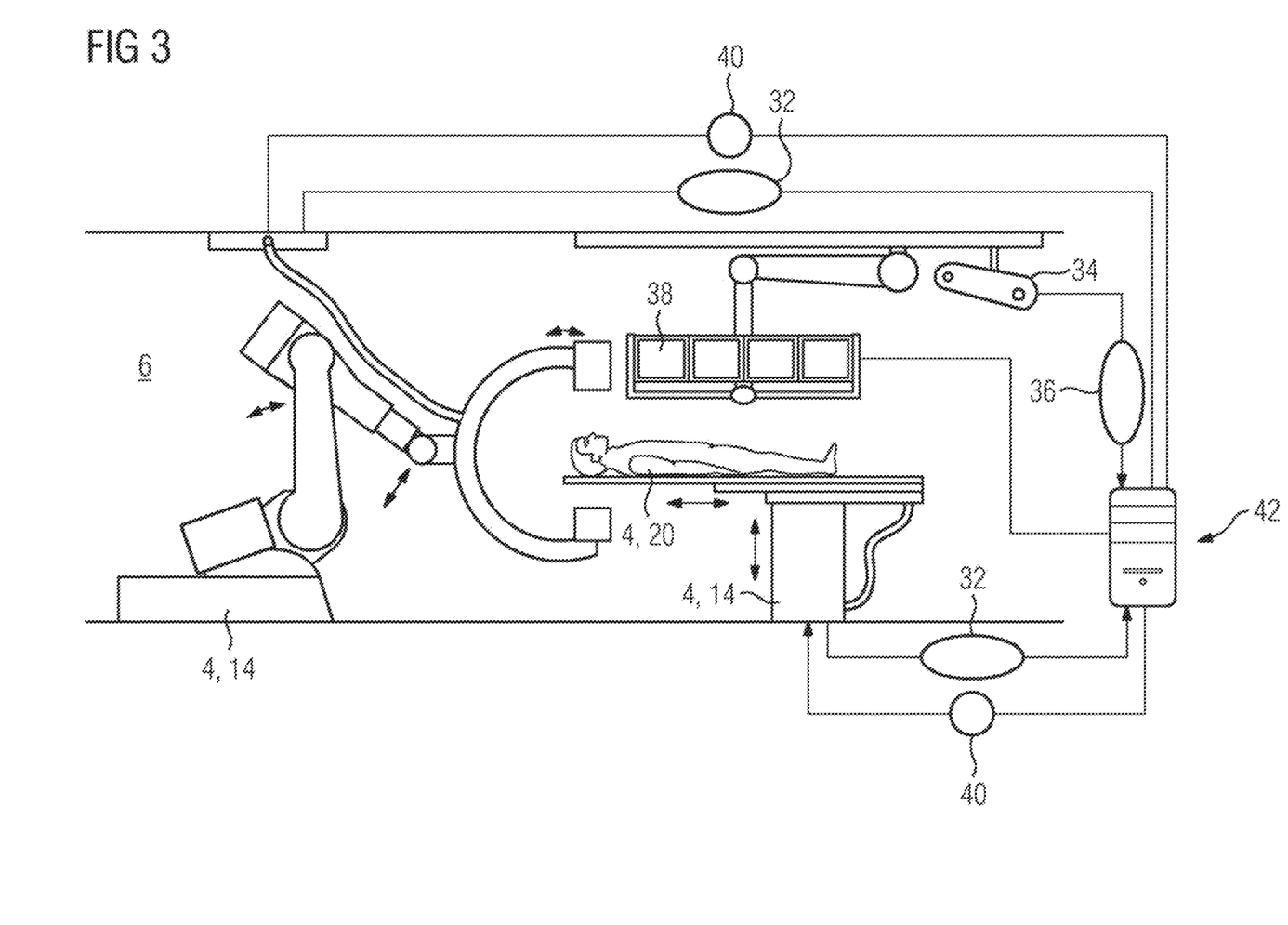
FIG. 3 schematically depicts an example of a procedure room and a number of medical devices, which are electronically configured according to a control signal output the device.

FIG. 3 illustrates the procedure room 6. In the procedure room, there is an x-ray c-arm and a patient table as medical devices 14, which are electronically configurable or moveable, which is indicated by the respective arrows. Therein, the x-ray c-arm as well as the patient table are connected to the device 42 and therefore configurable, (e.g., movable), according to the method M by the corresponding control signals 40.

The device 42 is depicted as a server. The server exemplarily is a single workstation. Alternatively, in one embodiment, the device includes one or more clustered computing devices.

The disclosure is not limited to the embodiments described above. Rather, other variants of the disclosure also be derived therefrom without departing from the scope of the disclosure. In particular, all the individual features described in connection with the exemplary embodiments may also be combined with one another in another manner without departing from the subject matter of the disclosure.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for acquiring and for altering a configuration of a plurality of objects in a procedure room for collision avoidance during a procedure, the method comprising:
    representing each object of the plurality of objects by a virtual model, each virtual model comprising a physical model of the object and a safety zone around the physical model, wherein the physical model represents a configuration of the object and the safety zone represents a collision-prevention area for a movement of any object of the plurality of objects during a procedure, and wherein each configuration of a respective object of the plurality of objects comprises a shape of the object, a position of the object, a position of a joint of the object, a velocity of a moving part of the object, an orientation of the object, or a relative position of a part of the object in relation to another part of the object;
    placing each virtual model of each object at a corresponding position in a virtual model of the procedure room;
    computing, by a controller, the configurations of the physical models during the procedure;
    determining, by the controller, a collision between objects during movement of an object of the plurality of objects based on an overlap of the safety zones of the respective physical models during the procedure; and
    avoiding the determined collision during the procedure by altering, by the controller, a plurality of configurations of respective physical models of corresponding objects affected by the determined collision.

2. The method of claim 1, wherein dimensions of the safety zone are varied during a movement of a respective physical model of an object of the plurality of objects.

3. The method of claim 1, wherein a physical model of a medical device is stored in a database,
    wherein the physical model of the medical device is retrieved for the computation when the medical device is registered, and
    wherein the corresponding virtual model represents one object of the plurality of objects in the procedure room.

4. The method of claim 3, wherein, during the procedure, a device signal is received, wherein the device signal comprises data about the configuration of the medical device, and
    wherein the configuration of the physical model of the medical device is set or altered according to the received device signal.

5. The method of claim 3, further comprising:
    generating, during the procedure, a control signal for control of the configuration of the medical device when a collision of the virtual model of the medical device in the computation is determined.

6. The method of claim 1, further comprising:
    deriving a virtual model of a patient from medical data; and
    positioning the virtual model of the patient in the virtual model of the procedure room, wherein the virtual model of the patient represents an object of the plurality of objects in the procedure room.

7. The method of claim 3, wherein the medical device is configured according to the corresponding virtual model.

8. The method of claim 1, further comprising:
displaying, on a display device, the virtual models of the plurality of objects and the procedure room.

9. A device for acquiring and for altering a configuration of a plurality of objects in a procedure room for collision avoidance during a medical procedure, the device comprising:
a controller configured to:
represent each object of the plurality of objects by a virtual model, each virtual model comprising a physical model of the object and a safety zone around the physical model, wherein the physical model represents a configuration of the object and the safety zone represents a collision-prevention area for a movement of any object of the plurality of objects during a procedure, and wherein each configuration of a respective object of the plurality of objects comprises a shape of the object, a position of the object, a position of a joint of the object, a velocity of a moving part of the object, an orientation of the object, or a relative position of a part of the object in relation to another part of the object;
place each virtual model of each object at a corresponding position in a virtual model of the procedure room;
compute the configurations of the physical models during the procedure
determine a collision between objects during movement of an object of the plurality of objects based on an overlap of the safety zones of the respective physical models during the procedure; and
alter a plurality of configurations of respective physical models of corresponding objects affected by the determined collision in order to avoid the determined collision during the procedure.

10. The device of claim 9, wherein at least one object of the plurality of objects is a medical device connected to the controller.

11. The device of claim 10, further comprising:
a tracking device configured to capture an object of the plurality of objects which is not connected to the controller and send a tracking signal comprising data about the configuration of the object to the controller.

12. The device of claim 9, further comprising:
a tracking device configured to capture an object of the plurality of objects which is not connected to the controller and send a tracking signal comprising data about the configuration of the object to the controller.

13. The method of claim 2, wherein a physical model of a medical device is stored in a database,
wherein the physical model of the medical device is retrieved for the computation when the medical device is registered, and
wherein the corresponding virtual model represents one object of the plurality of objects in the procedure room.

14. The method of claim 13, wherein, during the procedure, a device signal is received, wherein the device signal comprises data about the configuration of the medical device, and
wherein the configuration of the physical model of the medical device is set or altered according to the received device signal.

15. The method of claim 14, further comprising:
generating, during the procedure, a control signal for control of the configuration of the medical device when a collision of the virtual model of the medical device in the computation is determined.

16. The method of claim 15, further comprising:
deriving a virtual model of a patient from medical data; and
positioning the virtual model of the patient in the virtual model of the procedure room, wherein the virtual model of the patient represents an object of the plurality of objects in the procedure room.

17. The method of claim 16, wherein the medical device is configured according to the corresponding virtual model.

18. The method of claim 17, further comprising:
displaying, on a display device, the virtual models of the plurality of objects and the procedure room.

19. The method of claim 6, further comprising:
displaying, on a display device, the virtual models of the plurality of objects and the procedure room.

* * * * *

UNITED STATES PATENT AND TRADEMARK OFFICE
CERTIFICATE OF CORRECTION

PATENT NO. : 11,551,810 B2
APPLICATION NO. : 16/959221
DATED : January 10, 2023
INVENTOR(S) : Kerim Kara Page 1 of 1

It is certified that error appears in the above-identified patent and that said Letters Patent is hereby corrected as shown below:

On the Title Page

Item (71) Applicants:
"SIEMENS HEALTHCARE GMBH, Erlangen (DE); FRAUNHOFER GESELLSCHAFT ZUR FORDERUNG DER ANGEWANDTEN FORSCHUNG E.V., Mrinchen (DE)"

Should be replaced with:
"SIEMENS HEALTHCARE GMBH, Erlangen (DE); FRAUNHOFER GESELLSCHAFT ZUR FORDERUNG DER ANGEWANDTEN FORSCHUNG E.V., München (DE)"

Signed and Sealed this
Twenty-eighth Day of February, 2023

Katherine Kelly Vidal
*Director of the United States Patent and Trademark Office*